(12) United States Patent
Fujihara et al.

(10) Patent No.: US 11,393,086 B2
(45) Date of Patent: Jul. 19, 2022

(54) ULTRASONIC DIAGNOSTIC APPARATUS AND DISPLAY METHOD FOR ULTRASONIC INSPECTION

(71) Applicant: Hitachi, Ltd., Tokyo (JP)

(72) Inventors: Yoko Fujihara, Tokyo (JP); Maki Kuwayama, Tokyo (JP); Yoshiko Yamamoto, Tokyo (JP); Noriko Itabashi, Tokyo (JP)

(73) Assignee: FUJIFILM HEALTHCARE CORPORATION, Kashiwa (JP)

( * ) Notice: Subject to any disclaimer, the term of this patent is extended or adjusted under 35 U.S.C. 154(b) by 223 days.

(21) Appl. No.: 16/783,348

(22) Filed: Feb. 6, 2020

(65) Prior Publication Data
US 2020/0294226 A1    Sep. 17, 2020

(30) Foreign Application Priority Data
Mar. 11, 2019    (JP) .............................. JP2019-043315

(51) Int. Cl.
*G06T 7/00*    (2017.01)
*A61B 8/00*    (2006.01)

(52) U.S. Cl.
CPC .......... *G06T 7/0012* (2013.01); *A61B 8/4444* (2013.01); *G06T 2207/10132* (2013.01); *G06T 2207/20* (2013.01); *G06T 2207/30004* (2013.01); *G06T 2207/30204* (2013.01)

(58) Field of Classification Search
CPC ......... G06T 7/0012; G06T 2207/10132; G06T 2207/20; G06T 2207/30004; G06T 2207/30204; A61B 8/4444; A61B 8/42; A61B 8/5207; A61B 8/5223; A61B 8/461; A61B 8/0825; A61B 8/463; A61B 8/468; A61B 8/469; G01S 7/52073; G01S 7/52074; G01S 7/52098; G01S 15/8915; G01S 15/8936; G01S 15/899
See application file for complete search history.

(56) References Cited

U.S. PATENT DOCUMENTS

| | | | |
|---|---|---|---|
| 2006/0274928 A1* | 12/2006 | Collins | ................ A61B 6/5247 382/132 |
| 2015/0011858 A1* | 1/2015 | Caluser | .................... A61B 8/44 600/407 |

FOREIGN PATENT DOCUMENTS

| | | |
|---|---|---|
| JP | 2010-172499 A | 8/2010 |
| JP | 2014-014446 A | 1/2014 |
| JP | 2014-151208 A | 8/2014 |

OTHER PUBLICATIONS

Japanese Office Action and English Translation thereof for JP Appl. Ser. No. 2019-043315 dated Apr. 26, 2022 (8 pages).

* cited by examiner

*Primary Examiner* — Siamak Harandi
(74) *Attorney, Agent, or Firm* — Foley & Lardner LLP

(57) ABSTRACT

A main image includes a tomographic image and a reference image as ultrasonic images. A sub-image includes a site-of-interest map and a site-of-interest list. During execution of ultrasonic inspection, each time a new site of interest is identified, a site-of-interest symbol is added to the site-of-interest map and a site-of-interest record is added to the site-of-interest list. The position of the site-of-interest symbol is determined according to the position of a probe mark.

11 Claims, 9 Drawing Sheets

FIG. 2

| ID | TISSUE (ORGAN) | BODY MARK TYPE | BODY INFORMATION | | |
|---|---|---|---|---|---|
| | | | BODY HEIGHT | BODY WEIGHT | ... |
| 000001 | MAMMARY GLAND | MAMMARY GLAND 1 | **** | **** | ... |
| | | | | | |

FIG. 3

| INSPECTION SIDE | NUMBER | POSITION INFORMATION | | MEASUREMENT VALUE FIELD | | FINDING FIELD | | | COMMENT |
|---|---|---|---|---|---|---|---|---|---|
| | | x | y | MEASUREMENT 1 | ... | TYPE | SHAPE | ... | |
| Left | L1 | x1 | y1 | 13.0 | ... | CYST | round | ... | |
| | | | | | | | | | |

FIG. 4

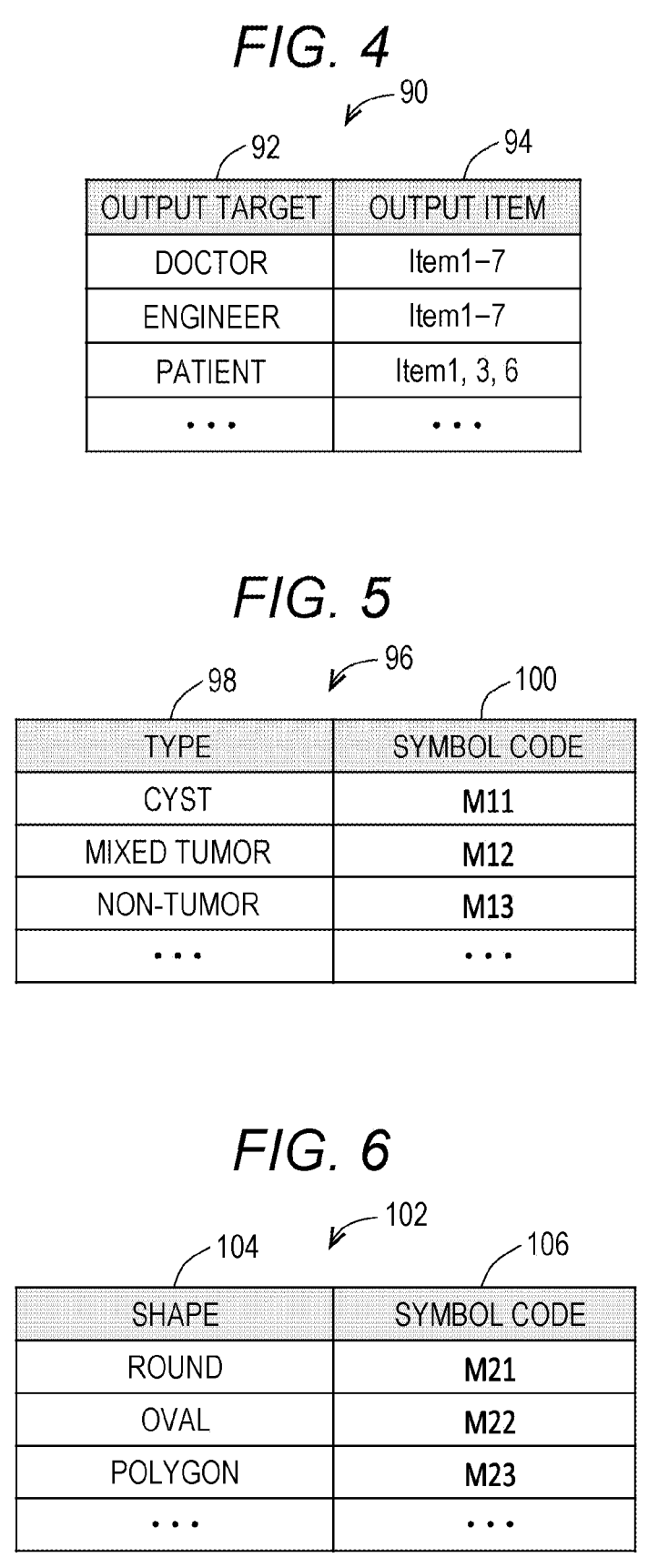

| OUTPUT TARGET | OUTPUT ITEM |
|---|---|
| DOCTOR | Item1-7 |
| ENGINEER | Item1-7 |
| PATIENT | Item1, 3, 6 |
| ... | ... |

FIG. 5

| TYPE | SYMBOL CODE |
|---|---|
| CYST | M11 |
| MIXED TUMOR | M12 |
| NON-TUMOR | M13 |
| ... | ... |

FIG. 6

| SHAPE | SYMBOL CODE |
|---|---|
| ROUND | M21 |
| OVAL | M22 |
| POLYGON | M23 |
| ... | ... |

| INSPECTION SIDE | NUMBER | POSITION INFORMATION | | | MEASUREMENT VALUE FIELD | | FINDING FIELD | | | IMAGE ANALYSIS RESULT | | COMMENT |
|---|---|---|---|---|---|---|---|---|---|---|---|---|
| | | X | Y | Z | MEASUREMENT 1 | ... | TYPE | SHAPE | ... | CATEGORY | ... | |
| Left | L1 | X1 | Y1 | Z1 | 13.0 | ... | CYST | round | ... | 2 | ... | |
| | | | | | | | | | | | | |

ULTRASONIC DIAGNOSTIC APPARATUS AND DISPLAY METHOD FOR ULTRASONIC INSPECTION

BACKGROUND OF THE INVENTION

1. Field of the Invention

The present invention relates to an ultrasonic diagnostic apparatus and a display method, and more particularly to a technique for supporting ultrasonic inspection.

2. Description of the Related Art

In an ultrasonic inspection of a target tissue such as breast, a site of interest such as a lesion site, a follow-up site, and the like is identified and evaluated by an inspector through observation of an ultrasonic image formed by an ultrasonic diagnostic apparatus.

Specifically, in the ultrasonic inspection, a site of interest is generally searched by manually moving an ultrasonic probe while observing the ultrasonic image. When the tissue of interest is found during the searching, a freeze operation is usually performed. A body mark and a probe mark are displayed next to the ultrasonic image. Before storing the ultrasonic image after freezing, the position and angle of the probe mark on the body mark are manually set according to the position and posture of the ultrasonic probe at the time of the freeze operation. Subsequently, the ultrasonic image including these marks is stored as an inspection report image. Before storing, the site of interest may be measured. In the ultrasonic inspection, a series of processing steps as described above are repeatedly performed for each site of interest.

After the ultrasonic inspection is completed, a paper inspection report or an electronic inspection report in which the inspection results by then are arranged or aggregated is created. Typically, in creating the inspection report, the position of the site of interest is entered on a schema (schematic diagram) representing the target tissue, and the findings of the inspector regarding the site of interest are entered. Note that the ultrasonic image may be stored as a moving image so that the ultrasonic inspection can be performed while reproducing the moving image.

SUMMARY OF THE INVENTION

Conventionally, performing the ultrasonic inspection and creating the inspection report are separate steps in which the latter step is performed after the former steps is done. In other words, it has not been possible to input the position, findings, and the like during the execution of the ultrasonic inspection for individual sites of interest which are identified sequentially. It has also been not possible to refer to a list of records or the like about the site of interest during the execution of the ultrasonic inspection.

JP 2010-172499 A describes a technique for creating an inspection report by mapping symbols on a schema. However, the technique creates an inspection report after execution of the ultrasonic inspection.

It is an object of the present invention to provide an inspector with an image in which an inspection result by then is displayed during ultrasonic inspection. It is another object of the present invention to enable input of information on each site of interest simultaneously with the ultrasonic inspection.

An ultrasonic diagnostic apparatus according to the present invention includes an ultrasonic image formation unit that forms an ultrasonic image representing a target tissue in accordance with a reception signal obtained by transmitting and receiving ultrasonic waves to and from the target tissue, an inspection record generation unit that generates an electronic inspection record including a site-of-interest map during execution of an ultrasonic inspection of the target tissue, and a display unit for displaying the ultrasonic image and the inspection record, in which the site-of-interest map includes a target tissue image representing the target tissue, and a site-of-interest symbol representing the site of interest identified by then during the execution of the ultrasonic inspection and displayed on the target tissue image, and the inspection record generation unit adds a new site-of-interest symbol to the site-of-interest map each time a new site of interest is identified during the execution of the ultrasonic inspection.

A display method according to the present invention includes forming an ultrasonic image representing a target tissue in accordance with a reception signal obtained by transmitting and receiving ultrasonic waves to and from the target tissue, generating an electronic inspection record including a site-of-interest map and a site-of-interest list during execution of an ultrasonic inspection of the target tissue, and displaying the ultrasonic image and the inspection record, in which a new site-of-interest symbol is added to the site-of-interest map and a new site-of-interest record is added to the site-of-interest list each time a new site of interest is identified during the execution of the ultrasonic inspection.

A program according to the present invention is a program executed by an information processing apparatus, the program including a function of forming an ultrasonic image representing a target tissue in accordance with a reception signal obtained by transmitting and receiving ultrasonic waves to and from the target tissue, and a function of generating an electronic inspection record including a site-of-interest map and a site-of-interest list during execution of an ultrasonic inspection of the target tissue, in which a new site-of-interest symbol is added to the site-of-interest map and a new site-of-interest record is added to the site-of-interest list each time a new site of interest is identified during the execution of the ultrasonic inspection.

According to an embodiment of the present invention, the image in which the inspection result by then is displayed can be provided to the inspector during the execution of the ultrasonic inspection. Alternatively, according to the embodiment of the present invention, the information on the site of interest can be input for each site of interest simultaneously with the ultrasonic inspection.

BRIEF DESCRIPTION OF THE DRAWINGS

FIG. 2 is an inspection management table;

FIG. 3 is an inspection result table;

FIG. 4 is an output management table;

FIG. 5 is a diagram illustrating a first example of a symbol management table;

FIG. 6 is a diagram illustrating a second example of the symbol management table;

FIG. 11 is an inspection result table according to the modification; and

DESCRIPTION OF THE PREFERRED EMBODIMENTS

Figure 1:
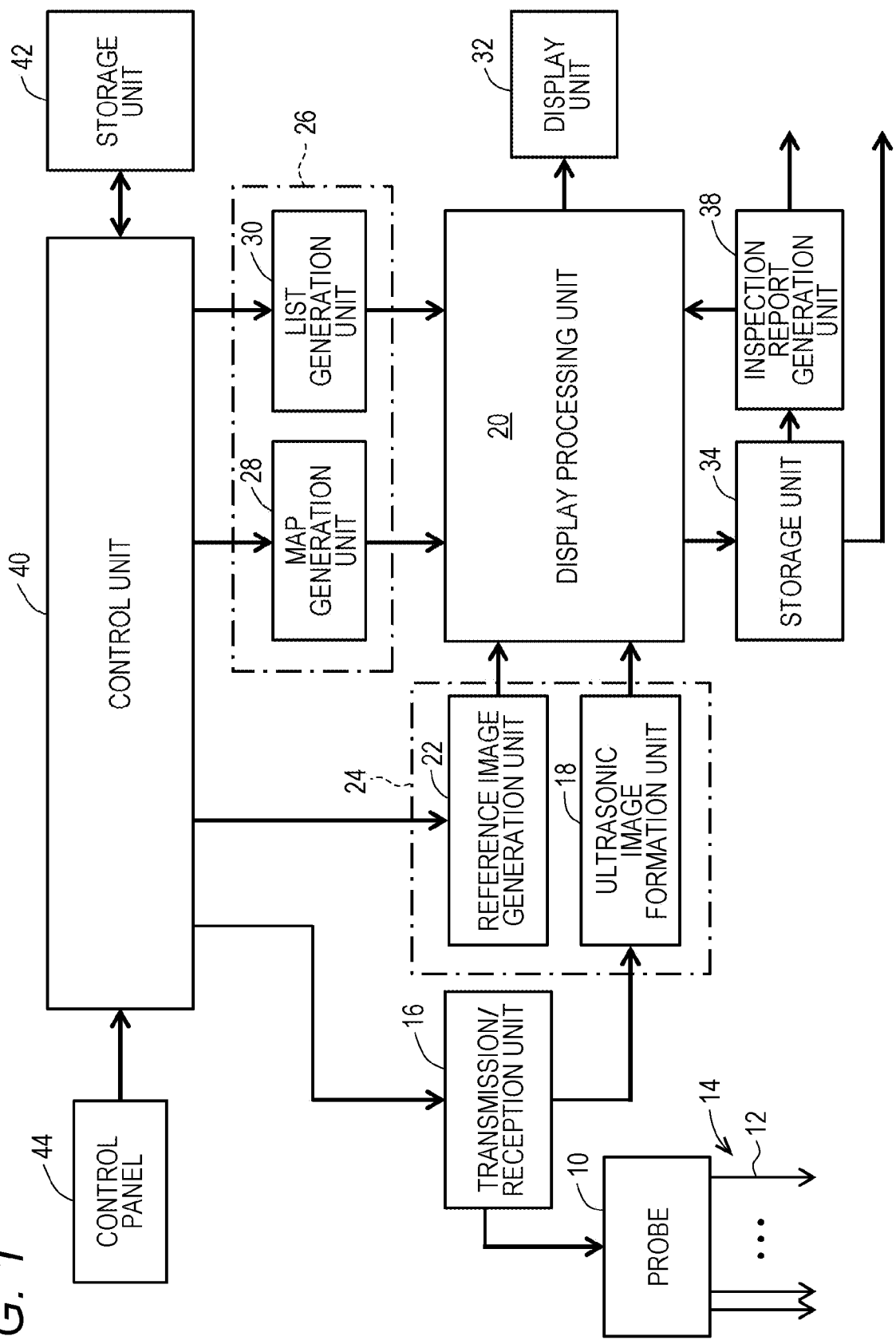
FIG. 1 is a block diagram illustrating an ultrasonic diagnostic apparatus according to an embodiment.

Hereinafter, embodiments will be described with reference to the accompanying drawings.

(1) Outline of the Embodiment

An ultrasonic diagnostic apparatus according to the embodiment includes an ultrasonic image formation unit, an inspection record generation unit, and a display unit. The ultrasonic image formation unit forms an ultrasonic image representing a target tissue on the basis of a reception signal obtained by transmitting and receiving ultrasonic waves to and from the target tissue. The inspection record generation unit generates an electronic inspection record including a site-of-interest map during execution of the ultrasonic inspection of the target tissue. The display unit displays an ultrasonic image and an inspection record. The site-of-interest map includes a target tissue image representing the target tissue and a site-of-interest symbol indicating the site of interest that has been identified by then during the execution of the ultrasonic inspection and displayed on the target tissue image. The inspection record generation unit adds a new site-of-interest symbol to the site-of-interest map each time a new site of interest is identified during the execution of the ultrasonic inspection.

With the above configuration, the contents of the site-of-interest map are updated each time a new site of interest is identified during the execution of the ultrasonic inspection. In other words, a new site-of-interest symbol is added to the site-of-interest map. By referring to the site-of-interest map during the execution of the ultrasonic inspection, it is possible to confirm the sites of interest identified by then or perform the subsequent ultrasonic inspection by taking such sites of interest into consideration. With the above configuration, the information to be included in the inspection report is input in advance, so that the inspection report can be created promptly after the ultrasonic inspection. In other words, the inspection report can be created or prepared simultaneously with the ultrasonic inspection.

Assume that the number of the sites of interest identified up to that point during the execution of the ultrasonic inspection is expressed by n, then the site-of-interest map includes n site-of-interest symbols displayed on the target tissue image. Here, n is an integer equal to or greater than 1, and n can increase during the execution of the ultrasonic inspection.

The above-described ultrasonic inspection includes a series of processes or steps for each site of interest (e.g., searching and identifying the site of interest, storing images, and the like). The series of processes or steps includes, for example, a freeze operation, a probe mark moving operation, measurement, and the like. Usually, when the site of interest is identified by observing the ultrasonic image, an inspector (user) performs the freeze operation. When a predetermined operation for identifying the site of interest, such as the freeze operation, a record adding operation, or the like, is performed, a new site-of-interest symbol may be displayed on the site-of-interest map or a state for accepting information on the new site of interest may be formed.

In the embodiment, the inspection record generation unit determines, on the basis of position information indicating the position of the new site of interest, a position at which the new site-of-interest symbol is added. With this configuration, the position of each site of interest identified by then can be known by referring to the site-of-interest map.

The ultrasonic diagnostic apparatus according to the embodiment displays a body mark, which schematically represents a target tissue, and a probe mark, which schematically represents an ultrasonic probe, are displayed together with the ultrasonic image. The position information indicates the position of the probe mark on the body mark.

With the above configuration, the display position of the site-of-interest symbol on the image of the target tissue is determined on the basis of the position of the probe mark on the body mark. The body mark and the probe mark are reference information for identifying the location at which the ultrasonic image is acquired when referring to the ultrasonic image later. In the above configuration, such reference information is used in generating the site-of-interest map. This reduces the burden of the inspector.

When the position of the probe mark is determined, the site-of-interest symbol may be displayed, or the site-of-interest symbol may be displayed before the probe mark is operated. In the latter case, when a certain operation is performed, the site-of-interest symbol is displayed at a temporary position, and then the site-of-interest mark moves in conjunction with the subsequent movement of the probe mark.

The position of the probe mark on the body mark is normally identified by the user, but it may be set automatically. The position of the site-of-interest symbol on the site-of-interest map may be determined on the basis of one or more of coordinate information of the ultrasonic probe, coordinate information identified by analysis of the ultrasonic image, and coordinate information identified by measurement of the ultrasonic image. Alternatively, coordinates of the symbol on the site-of-interest map may be directly designated by the inspector.

In the ultrasonic diagnostic apparatus according to the embodiment, the ultrasonic image and the inspection record are displayed side by side in a predetermined direction on the screen, and the body mark and the probe mark are displayed on the side closer to the inspection record of one side or the other side of the ultrasonic image in the predetermined direction. With this configuration, it is easy to shift the line of sight to the ultrasonic image and the inspection record image when observing the reference image including two marks. Alternatively, it becomes easy to compare the reference image to the inspection record.

If the position of the site-of-interest symbol is dynamically changed in conjunction with the change of position of the probe mark, while being changed, then the correspondence between the probe mark and the site-of-interest symbol can easily be recognized.

In the embodiment, a plurality of symbol forms representing a plurality of tissue characteristics is prepared, and a specific symbol form corresponding to the tissue characteristics of the site of interest is selected from among the plurality of symbol forms for each site-of-interest symbol. With this configuration, it is possible to recognize the tissue characteristic of the site of interest represented by the site-of-interest symbol through observation.

In the embodiment, the inspection record further includes a site-of-interest list, and the inspection record generation unit adds a new site-of-interest record to the site-of-interest list each time a new site of interest is identified during the execution of the ultrasonic inspection. With this configuration, it is possible to recognize, by referring to the site-of-interest map and the site-of-interest list, the position and the inspection result for each site of interest identified by then.

In the embodiment, the site-of-interest record includes findings entered by the inspector. With this configuration, it is possible to effectively create the inspection report while performing the ultrasonic inspection. In addition, the findings that have been input by then are referred to during the ultrasonic inspection, so that the subsequent ultrasonic inspection can be performed by taking such information into consideration. For example, it is possible to identify the site where the ultrasonic inspection has not performed or the site where the ultrasonic inspection is to be performed next.

When the inspector operates to add the site of interest, a state for receiving information such as the position and form of the site-of-interest symbol is formed and, at the same time, a state for receiving information such as findings constituting the site-of-interest record may be formed. In any case, each time a new site of interest is identified, the site-of-interest map is updated and the site-of-interest list is updated. Some information may be entered afterwards.

A display method according to the embodiment includes forming an ultrasonic image representing a target tissue on the basis of a reception signal obtained by transmitting and receiving ultrasonic waves to and from the target tissue, generating an electronic inspection record including a site-of-interest map and a site-of-interest list during execution of an ultrasonic inspection of the target tissue, and displaying the ultrasonic image and the inspection record. Each time the new site of interest is identified during the execution of the ultrasonic inspection, the new site-of-interest symbol is added to the site-of-interest map and the new site-of-interest record is added to the site-of-interest list.

According to the above display method, the ultrasonic inspection can be performed while referring to the site-of-interest map and the site-of-interest list that are updated in stages, so that the accuracy and efficiency of the ultrasonic inspection can be improved. In addition, the information about the site is recorded each time the site of interest is identified, so that it is possible to more efficiently create the inspection report. In other words, the display method comprehensively supports ultrasonic inspection.

The display method may be implemented as a software function or a hardware function. In the former case, a program for executing the display method is installed in an information processing apparatus via a network or a portable storage medium. The concept of the information processing apparatus can include an ultrasonic diagnostic apparatus, an image processing apparatus, a computer, and the like.

(2) Details of the Embodiment

FIG. 1 illustrates an ultrasonic diagnostic apparatus according to the embodiment. The ultrasonic diagnostic apparatus is a medical apparatus installed in a medical institution such as a hospital to form and display the ultrasonic image by transmitting and receiving ultrasonic waves to and from a living body. In the embodiment, the target tissue of the ultrasonic inspection is, for example, a tissue of the breast.

An ultrasonic probe 10 includes a 1D vibration element array in the illustrated configuration example. The 1D vibration element array includes a plurality of vibration elements arranged linearly or in an arcuate shape. The 1D vibration element array generates ultrasonic beams 12, and the ultrasonic beams 12 scan electronically to generate a beam scanning plane 14 as a two-dimensional data capturing area. A 2D vibration element array may be provided instead of the 1D vibration element array. The ultrasonic probe 10 is a living body contact type ultrasonic probe. Instead, it is also possible to use a body cavity insertion type ultrasonic probe.

A transmission/reception unit 16 includes a transmission circuit and a reception circuit. The transmission circuit functions as a transmission beam former. The reception circuit functions as a reception beam former. At the time of transmission, a plurality of transmission signals is supplied in parallel from the transmission circuit to the 1D vibration element array. As a result, the 1D vibration element array generates the transmission beams. At the time of reception, a plurality of reception signals output in parallel from the 1D vibration element array enters the reception circuit. In the reception circuit, a plurality of reception signals is subjected to phased addition (delayed addition) to generate beam data corresponding to the reception beams.

Note that frame data is made of a plurality of pieces of beam data arranged in a direction of electronic scanning. Electronic scanning is performed repeatedly to sequentially generate the plurality of frame data pieces. The beam data is individually formed by a plurality of pieces of echo data arranged in a depth direction. A beam data processing circuit provided at the subsequent stage of the transmission/reception unit 16 is not illustrated.

A control unit 40 includes a central processing unit (CPU) and an operation program. The control unit 40 controls the operation of each element constituting the ultrasonic diagnostic apparatus. In particular, the control unit 40 according to the embodiment controls generation of a main image and a sub-image, as will be described later. An operation panel 44 is connected to the control unit 40. The operation panel 44 is an input device including a plurality of switches, a plurality of buttons, a trackball, a keyboard, and the like. A storage unit 42 is connected to the control unit 40. The storage unit 42 stores an inspection management table, an inspection result table, an output management table, a symbol management table, and the like, all of which will be described later. The storage unit 42 includes a semiconductor memory, a hard disk, and the like.

The ultrasonic image formation unit 18 is an electronic circuit that sequentially forms ultrasonic images on the basis of frame data input sequentially. In the embodiment, the ultrasonic image is a tomographic image. The ultrasonic image formation unit 18 includes a digital scan converter (DSC). The DSC has a coordinate conversion function, a pixel interpolation function, a frame rate adjustment function, and the like. Data representing the tomographic image is sent from the ultrasonic image formation unit 18 to the display processing unit 20.

The reference image generation unit 22 is a module that generates a reference image to be displayed together with the tomographic image. The reference image includes a body mark schematically illustrating the target tissue and a probe mark schematically illustrating the ultrasonic probe. A plurality of body marks corresponding to a plurality of target tissues is prepared, and a specific body mark corresponding to an actual target tissue is selected from the plurality of body marks. The selection is made by the inspector or automatically. The probe mark is a mark indicating the position of ultrasonic diagnosis, that is, the contact position of the ultrasonic probe or the position of the scanning plane. The position and orientation are usually set by the inspector.

At that time, an operation panel 44 is used. The setting of the probe mark may be automated.

The probe mark includes graphic indicating a start point of the electronic scanning. When referring to the ultrasonic image later, the position of a cross section of the tissue appearing on the ultrasonic image is identified from the position of the probe mark on the body mark. Reference image data is sent from the reference image generation unit 22 to the display processing unit 20.

In the embodiment, the main image and the sub-image are displayed on the same screen when the ultrasonic inspection support mode is executed. The main image is formed by an ultrasonic image and a reference image. The sub-image is an image corresponding to the inspection record or includes the inspection record as content. The inspection record is formed by a site-of-interest map and a site-of-interest list. As illustrated in FIG. 1, the main image generation unit 24 includes the ultrasonic image formation unit 18 and the reference image generation unit 22, both of which have been described. On the other hand, the sub-image generation unit 26 includes a map generation unit 28 and a list generation unit 30 as described below. The reference image generation unit 22, the map generation unit 28, and the list generation unit 30 may be implemented as functions exhibited by the CPU, or may be configured by a dedicated processor.

The map generation unit 28 is a module that generates a site-of-interest map. The site-of-interest map includes a scheme image as a target tissue image and n site-of-interest symbols indicating the identified n sites of interest. n is an integer equal to or greater than 1, and n may increase during the execution of the ultrasonic inspection. The map generation unit 28 adds a new site-of-interest symbol to the site-of-interest map each time a new site of interest is identified during the execution of the ultrasonic inspection. In the configuration example illustrated in FIG. 1, a position where the site-of-interest symbol overlaps in the scheme image is determined on the basis of the position of the probe mark on the body mark.

The list generation unit 30 is a module that generates the site-of-interest list. The site-of-interest list is formed by n site-of-interest records corresponding to the identified n sites of interest. Each site-of-interest record includes information indicating the position of the site of interest, findings input by the inspector, and the like. The findings are opinion or comment by the inspector who has monitored the site of interest. The site-of-interest map and the site-of-interest list may be referred to as information constituting the inspection report.

The display processing unit 20 has an image synthesizing function, a color processing function, and the like. The display processing unit 20 generates a display image to be displayed on the screen of the display device 32. The display image displayed during the execution of the ultrasonic inspection includes the main image and the sub-image as described above. The display processing unit 20 is implemented, for example, as a function exhibited by the CPU, or includes a dedicated processor. The display device 32 is implemented, for example, as a liquid crystal display device, an organic electroluminescence (EL) display device, or the like.

The storage unit 34 stores an ultrasonic image and a reference image to be stored, and stores the inspection record (i.e., the site-of-interest map and the site-of-interest list) which is updated in stages. The storage unit 34 is implemented as a semiconductor memory, a hard disk, or the like.

The inspection report generation unit 38 is a module that generates an electronic inspection report on the basis of information stored in the storage unit 34 and the storage unit 42. The inspection report generation unit 38 may be implemented as a function exhibited by the CPU or may be configured with a dedicated processor. The inspection report is displayed on the display device 32 and transferred to an external device via a network as necessary. Information stored in the storage unit 34 and the storage unit 42 may be transferred to an external device.

Examples of the ultrasonic image include a Doppler color image, an elastography image, and the like, in addition to the tomographic image described above. The main image may be displayed on the main display and the sub-image may be displayed on the sub-display, but preferably both the main image and the sub-image are displayed on the same screen.

FIG. 2 illustrates an inspection management table. The illustrated inspection management table 50 includes a plurality of records 52. Each record 52 includes a plurality of pieces of information, such as a patient ID 54, a target tissue 56, a body mark type 58, body information 60, and the like. An inspection identification (ID) may be managed instead of the patient ID 54. The target tissue 56 is a tissue subjected to the ultrasonic inspection. The body mark type 58 is information for designating a body mark form corresponding to the target tissue 56. The body information 60 includes a body height 62, a body weight 64, and the like. By referring to the inspection management table 50, the type of ultrasonic inspection, the type of body mark, and the like are identified.

FIG. 3 illustrates an inspection result table. The inspection result table 66 illustrated includes a plurality of records 68. Individual records 68 correspond to individual sites of interest in the illustrated example. Each record 68 includes a plurality of pieces of information including information 70 for identifying the inspection side (right side or left side), a site-of-interest number 72, position information 74, a measurement value field 76, a finding field 78, a comment field 88, and the like. For example, when the target site is the breast, it is identified on the basis of the information 70 as to whether the inspection target is the right breast or the left breast. Each time the site of interest is identified, a new record 68 with a new site-of-interest number 72 is generated.

The position information 74 is information indicating the position (specifically, the display position or the superimposed position) of the site-of-interest symbol on the scheme image in the configuration example illustrated in FIG. 1. For example, the position may be the center position of the site-of-interest symbol. The schematic diagram has a coordinate system, and the position information 74 indicates relative coordinates in the coordinate system of the schematic diagram. Specifically, the display position of the site-of-interest symbol is configured with an x-coordinate and a y-coordinate.

In the embodiment, assuming that the coordinate system of the body mark and the coordinate system of the scheme image are associated with each other, position information in the former coordinate system is used as position information in the latter coordinate system. Alternatively, the position information in the former coordinate system is converted into position information in the latter coordinate system. Note that the position of the probe mark is, for example, the center position of the probe mark. In displaying the site-of-interest symbol, the orientation (i.e., angle) of the probe mark may be used.

During the execution of the ultrasonic inspection, a freeze operation is usually performed for the identified site of interest. After the freeze operation, the position and angle of the probe mark are adjusted on the body mark before storing the ultrasonic image. Upon completion of the adjustment, the position information 74 is identified or calculated on the basis of the position of the body mark.

In the measurement value field 76, the result of measurement performed on the site of interest (i.e., measurement value) is stored. For example, when the length is measured, numerical information indicating the length is recorded. When the area is measured, numerical information indicating the area is recorded. When multiple measurements are executed, measurement values are recorded in the measurement value field 76. In the finding field 78, the result of observation by the inspector is recorded. For example, information such as the tissue type 80 and the tissue shape 82 is recorded. The form of the target tissue symbol may be automatically determined according to the tissue type 80, the tissue shape 82, and the like. The comment field 88 is a field for recording other information that cannot be recorded in the finding field 78.

The record 68 is added to the inspection result table 66 as the site of interest is sequentially identified in accordance with the progress of the ultrasonic inspection. On the basis of the updated inspection result table 66, the site-of-interest map and the site-of-interest list are updated.

FIG. 4 illustrates an output management table. The illustrated output management table 90 is a table for identifying an output item 94 for each output target 92. For example, all output items are designated for creating an inspection report to be presented to a doctor or an engineer. In creating the inspection report to be presented to the patient, some output items are designated. The output management table 90 is referred to by the inspection report generation unit illustrated in FIG. 1.

FIG. 5 illustrates a first example of a symbol management table. In the illustrated example, a symbol management table 96 manages symbol codes 100 by organization type 98 indicating tissue characteristics. When a specific tissue type is designated, a corresponding symbol code is selected. A form of the symbol is determined for each symbol code.

FIG. 6 illustrates a second example of the symbol management table. In the illustrated example, a symbol management table 102 manages symbol codes 106 by tissue shape indicating the tissue characteristics. When a specific tissue shape is designated, a corresponding symbol code is selected. A form of the symbol is determined for each symbol code. The symbol management tables illustrated in FIGS. 5 and 6 are referred to by the map generation unit illustrated in FIG. 1.

Figure 7:
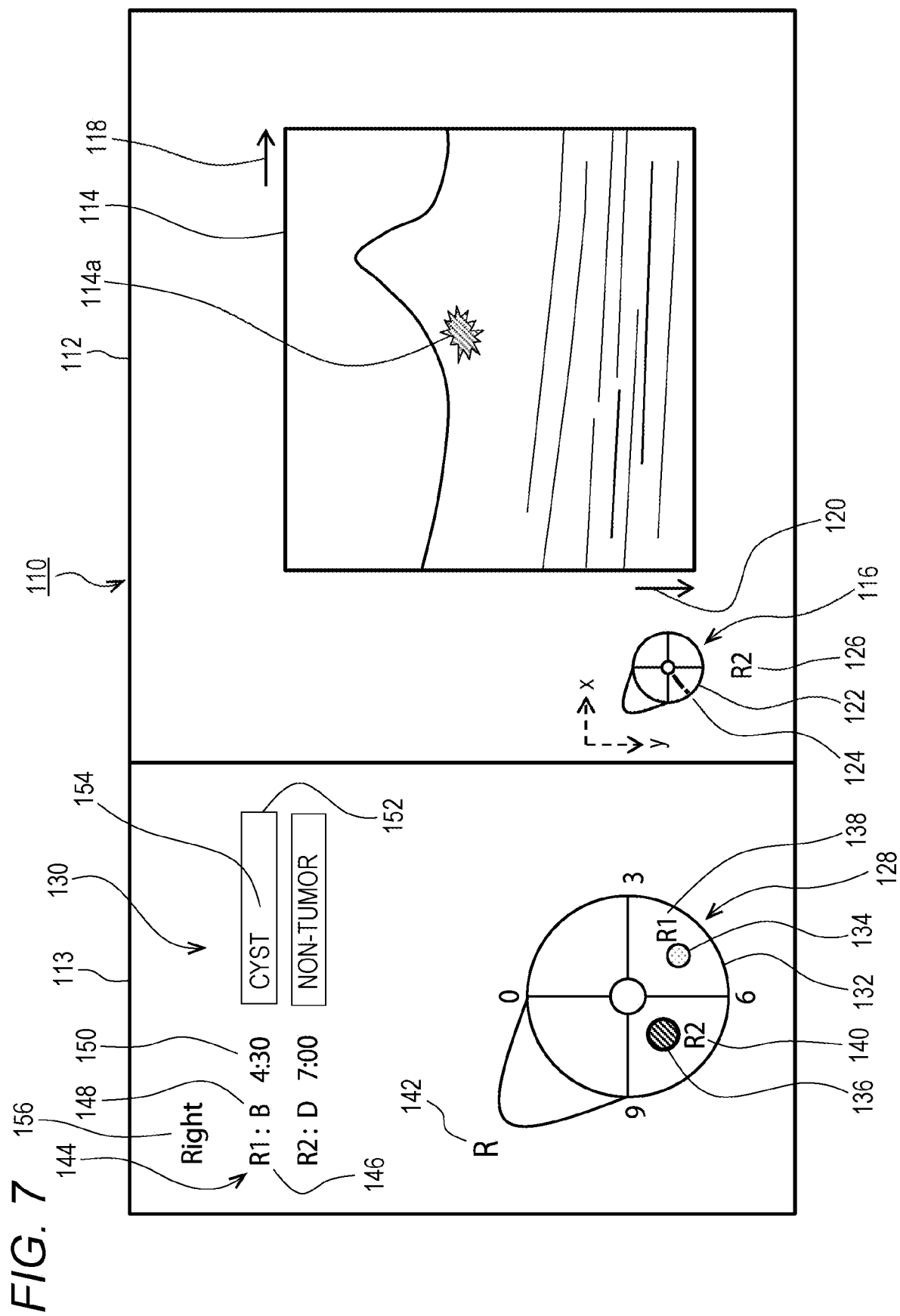
FIG. 7 is a display example.

FIG. 7 illustrates an image displayed during execution of an ultrasonic inspection support mode. The image 110 includes a main image 112 and a sub-image 113 arranged horizontally (i.e., laterally).

The main image 112 includes a tomographic image 114 as an ultrasonic image and a reference image 116 as a graphic image. In the illustrated example, a lateral direction 118 in the tomographic image 114 is an electronic scanning direction, and a vertical direction 120 in the tomographic image 114 is a depth direction. When the sector scanning or the convex scanning is adopted, a fan-shaped ultrasonic image is displayed. A position of the scanning plane changes according to the position and posture of the ultrasonic probe on the breast, and the content of the tomographic image changes accordingly. In the ultrasonic inspection, the position and posture of the ultrasonic probe are changed, while observing a tomographic image as a moving image, to search the site of interest such as a lesion site, a follow-up site, or a healing site.

In the example illustrated in FIG. 7, a site of interest 114a appears in the tomographic image 114. When the site of interest 114a is found, a freeze operation is typically performed. This stops transmission/reception, and the tomographic image becomes a still image. In this state, it is also possible to sequentially reproduce the frame sequence stored in the cine memory as a ring buffer.

The reference image 116 is displayed on the side closer to the sub-image 113 on one side or the other side of the tomographic image 114. The reference image 116 includes a body mark 122 and a probe mark 124. In the illustrated example, the body mark 122 schematically illustrates the right breast. Usually, in the frozen state, the inspector changes the position and orientation of the probe mark 124. In that case, the position and orientation of the probe mark 124 are manually set so that the position and orientation of the ultrasonic probe at the time when the displayed tomographic image 114 is acquired are reproduced. In that case, the above-described operation panel is used. The body mark 122 or the reference image 116 including the body mark 122 has its own coordinate system which is represented by x and y in FIG. 7. The position of the probe mark 124 is identified as the x coordinate and the y coordinate. The illustrated reference image 116 includes a site-of-interest number 126 representing a site of interest identified at the current time.

The sub-image 113 includes a site-of-interest map 128 and a site-of-interest list 130. The site-of-interest map 128 includes a scheme image 132 representing the target tissue and n site-of-interest symbols 134 and 136. In the embodiment, the scheme image 132 and the body mark 122 have the same content. Alternatively, the content may be different. In the embodiment, the scheme image 132 is a graphic image that schematically represents the right breast in the embodiment. Instead of the scheme image 132, a target tissue image such as graphic, an anatomical chart, a photograph, or an actual image may be displayed.

The illustrated site-of-interest map 128 includes a plurality of site-of-interest numbers 138 and 140 displayed adjacent to the plurality of site-of-interest symbols 134 and 136, respectively. Both symbols are identifiers. The form (e.g., shape, color, or the like) of the site-of-interest symbols 134 and 136 represents one or both of the type and form of the site of interest. The site-of-interest map 128 includes a plurality of numbers indicating orientations. In addition, an index 142 indicating the right side is included. In a situation where a new site of interest is currently identified, when the probe mark 124 is moved, the site-of-interest symbol 136 also moves. The display position of the site-of-interest symbol 136 is determined by the final position set for the probe mark 124.

The site-of-interest list 130 includes n site-of-interest records 144 corresponding to the n sites of interest identified by then. Each site-of-interest record 144 is the site-of-interest information provided as a list element, and specifically includes a site-of-interest number 146, position information, and a finding field 152. Specifically, the position information includes an area number 148 where the center coordinates of the site-of-interest symbol exist, and an orientation 150 in which the center coordinates are directed. The scheme image 132 is divided into a plurality of areas, and each area is identified by the area number 148. The orientation 150 is identified following the clock face. In the finding field 152, a specific tissue type 154 selected from a plurality of tissue types is displayed.

In other words, when there is an operation for identifying the site of interest, or when there is an instruction to add a record of the site of interest, a state for accepting information about a new site-of-interest symbol and a state for accepting information that constitutes a new site of interest is generated. For example, at that time, a new site-of-interest symbol having a temporary form is added to a temporary position on the site-of-interest map 128. At that time, a site-of-interest record in which information is partially missing in the site-of-interest list 130 is added. After that, on the basis of information (including probe mark position information, form information, and findings) input by the inspector, the position and form of the site-of-interest symbol are determined, and the content of the site-of-interest record is supplemented. After all necessary information has been received, the site-of-interest symbol and the site-of-interest record may be added. The provisional position may be determined on the basis of the current position of the probe mark.

The freeze operation or the probe mark operation may be regarded as a site-of-interest adding operation. Apart from such operations, a symbol adding operation and a record adding operation may be accepted separately. In any case, each time a new site of interest is identified, the site-of-interest map and the site-of-interest list are updated as a result. When the freeze operation is released, it is determined that the site-of-interest adding processing is ended and, simultaneously, the state for waiting for a new site-of-interest adding operation may be formed. In the frozen state, the site of interest is measured as necessary.

In the frozen state, a tomographic image is stored. Subsequently, when the freeze is released, transmission/reception resumes, and the tomographic image becomes a moving image. In this state, a new site of interest is searched for by adjusting the position and posture of the ultrasonic probe while observing the tomographic image. When the new site of interest is identified, the above-described series of steps is performed. When the ultrasonic inspection is completed, an inspection report is generated and output. In that case, information identified or inputted in the process of ultrasonic inspection is used.

Figure 8:
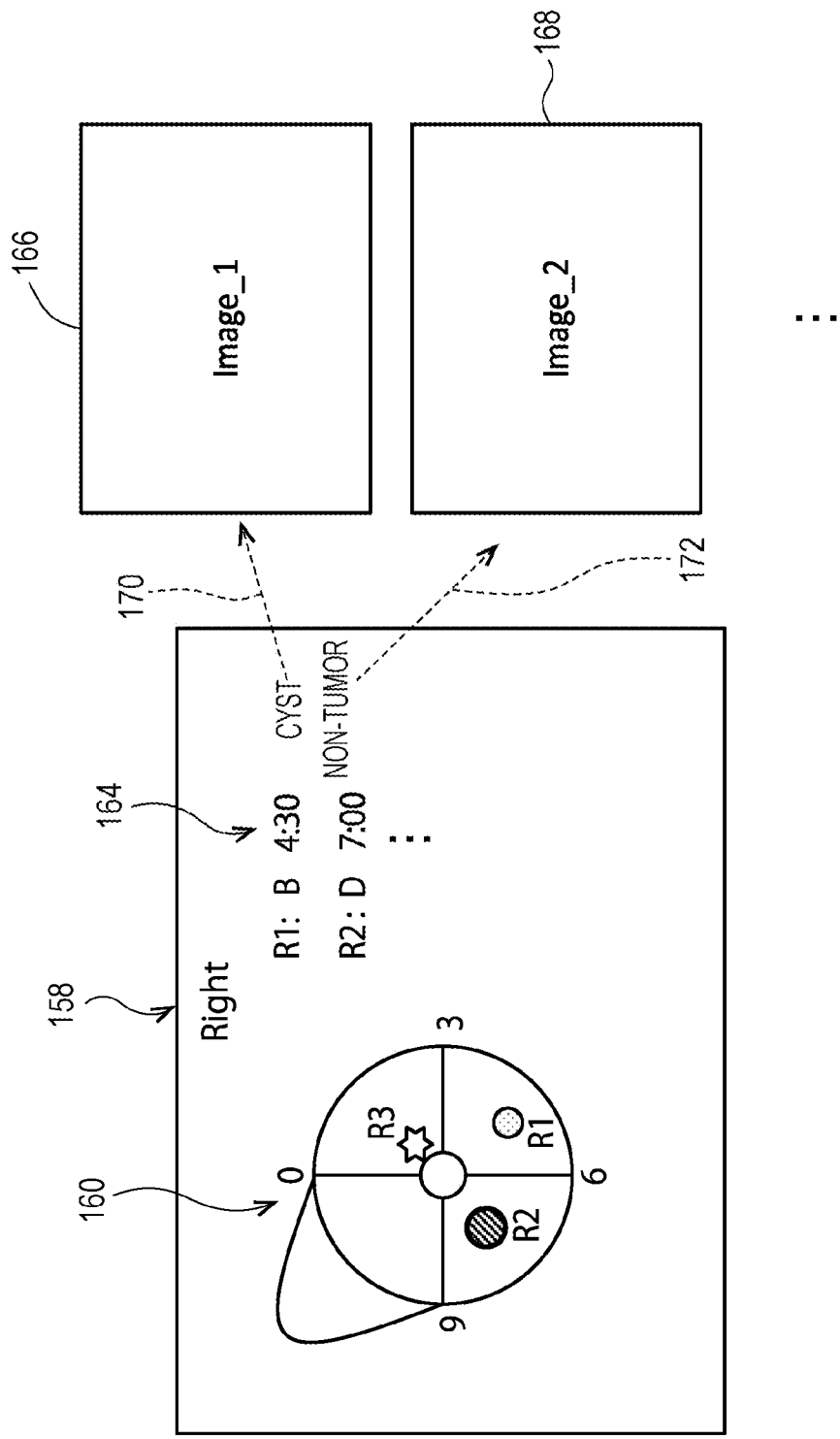
FIG. 8 is an example of a simple inspection report.

FIG. 8 illustrates an inspection report. An inspection report 158 illustrated is a simple inspection report. The inspection report 158 includes a site-of-interest map 160 and a site-of-interest list 164 that have been created through the ultrasonic inspection step. As indicated by reference numerals 170 and 172, a plurality of tomographic images 166 and 168 may be associated with a plurality of sites of interest. According to such a configuration, a tomographic image corresponding to the site-of-interest record or symbol selection can be automatically reproduced. A more detailed inspection report may be generated in the ultrasonic diagnostic apparatus or in another apparatus.

Figure 9:
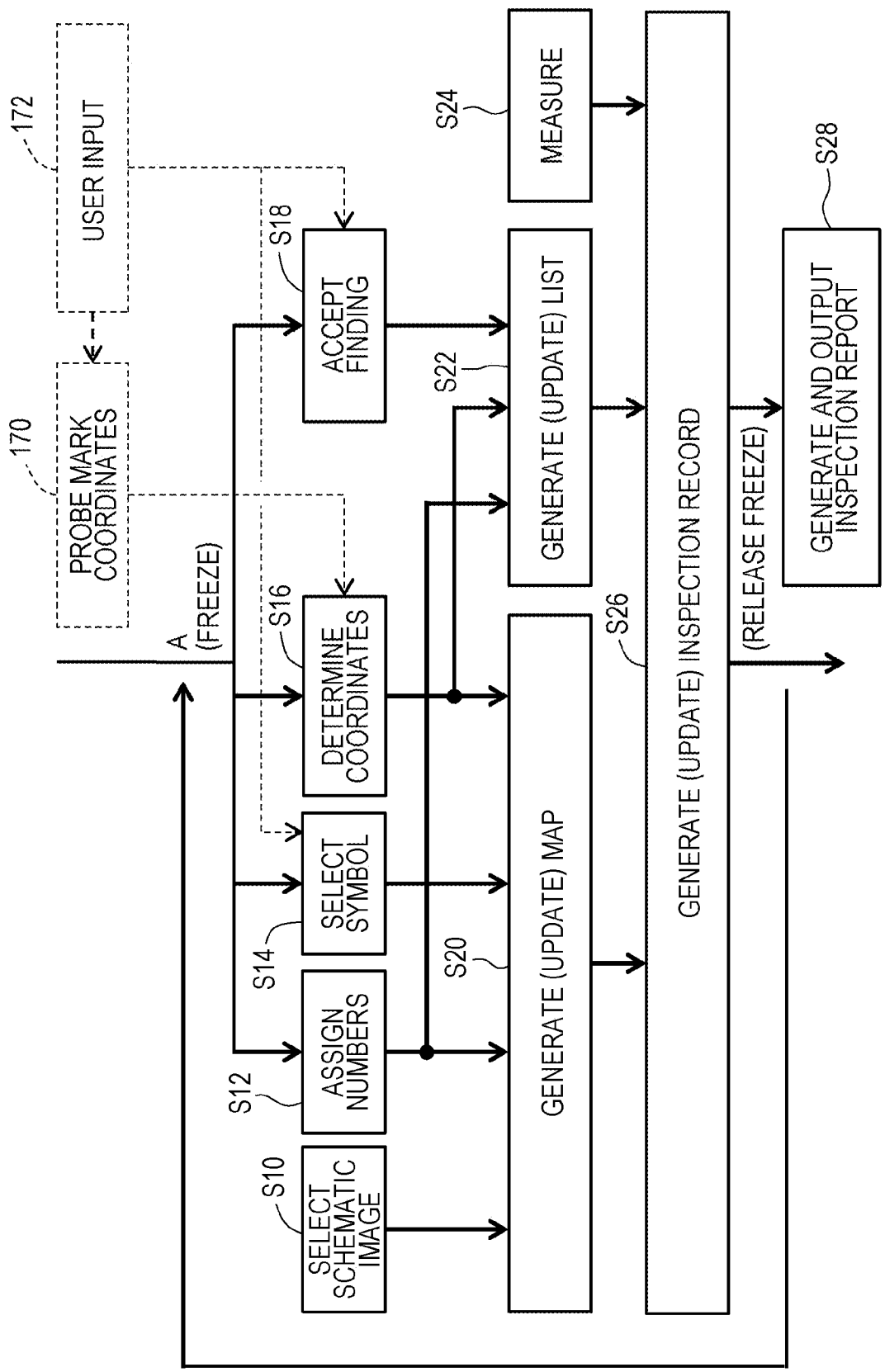
FIG. 9 is a flowchart illustrating an operation of the ultrasonic diagnostic apparatus according to the embodiment.

Next, an operation example of the ultrasonic diagnostic apparatus illustrated in FIG. 1 will be described with reference to FIG. 9. In the process of ultrasonic inspection, the processing steps after A is executed each time the site of interest to be recorded is identified by observing the ultrasonic image.

In S10, a scheme image is selected. A scheme image is selected according to the target tissue of the ultrasonic inspection. In that case, the inspection management table described above may be referred to. In the embodiment, S10 is executed only once at the start of execution of the ultrasonic inspection.

In S12, the site-of-interest number is assigned to the newly identified site of interest. In S14, the form of the site-of-interest symbol is selected. In S16, the display coordinates of the site-of-interest symbol are determined on the basis of the probe mark coordinates designated by the user (see reference numerals 172 and 170). Meanwhile, the inspector enters the finding about the site of interest (see reference numeral 172) and the finding is accepted in S18. On the basis of the input findings, the symbol form may be selected in S14.

In S20, a site-of-interest map is generated (or updated). In S22, a site-of-interest list is generated (or updated). In S24, measurement for the site of interest is performed. In S26, the sub-image is displayed together with the main image. The sub-image includes the site-of-interest map and the site-of-interest list as the inspection records. Subsequently, when the freeze is released, the processing steps from A are repeated. When the ultrasonic inspection process is completed, the inspection report is created and output in S28.

In the embodiment, concurrently with the ultrasonic inspection, the record such as a position, findings, and the like of the site of interest can be performed. In addition, an inspection record corresponding to the inspection history can be referred to at the time of ultrasonic inspection, and its content can be used for the subsequent ultrasonic inspection. Since all or a part of information constituting the inspection report can be identified or input while performing the ultrasonic inspection, the efficiency of generating the inspection report can be improved. Furthermore, in the configuration example described above, the position of the site-of-interest symbol is automatically determined on the basis of the position of the probe mark, so that the burden of the inspector can be reduced compared to the case where the position of the site-of-interest symbol is identified by the inspector.

Figure 10:
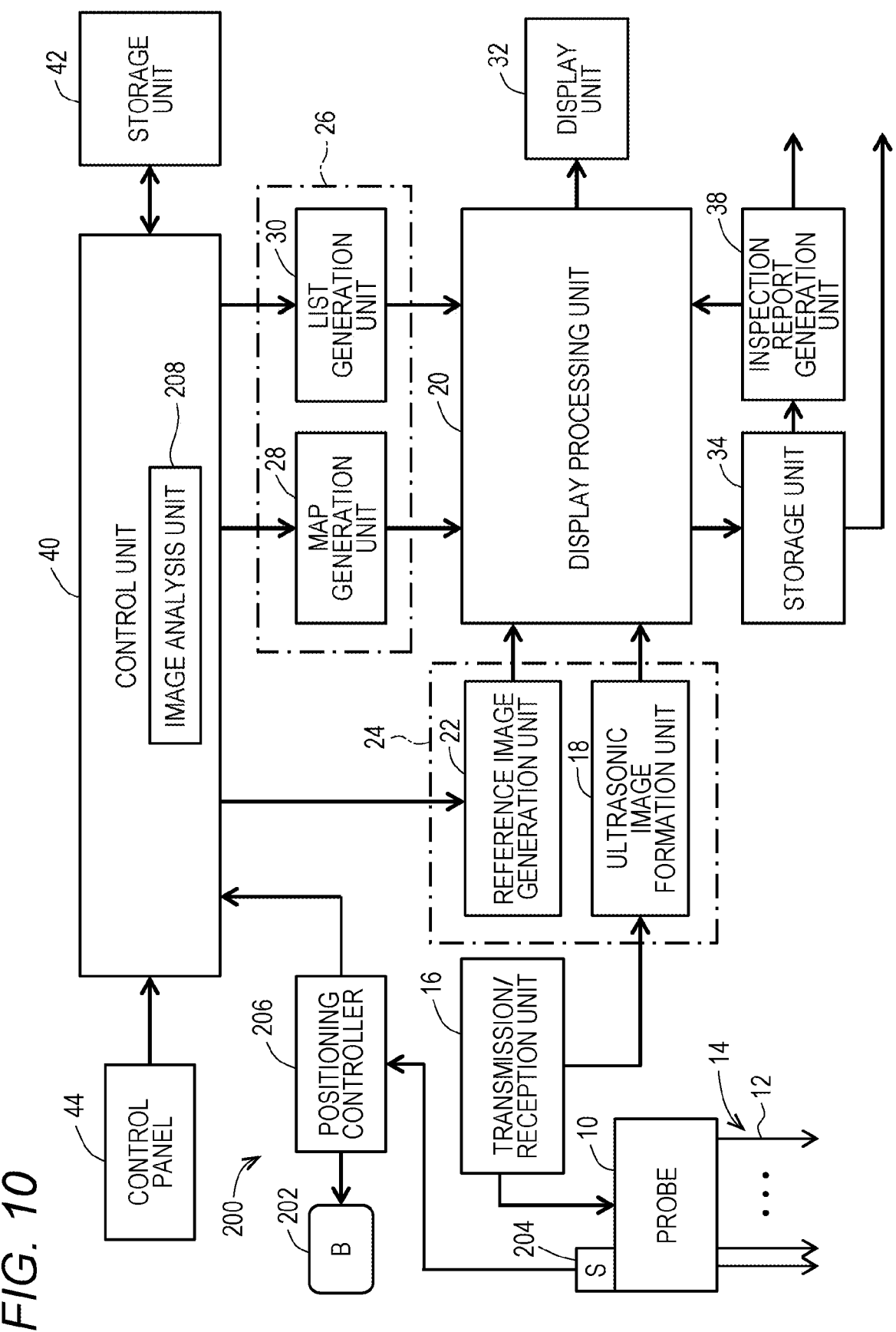
FIG. 10 is a block diagram illustrating an ultrasonic diagnostic apparatus according to a modification.

A modification will be described with reference to FIGS. 10 to 12. FIG. 10 illustrates an ultrasonic diagnostic apparatus according to a modification. The same reference sings are given to the constituent elements similar to those that have already been described and the description thereof will not be repeated. The same applies to FIGS. 11 and 12 described later.

An ultrasonic diagnostic apparatus illustrated in FIG. 10 includes a positioning system 200. The positioning system 200 includes a magnetic field generator 202, a magnetic sensor 204, and a positioning controller 206. The magnetic sensor 204 is attached to the probe head of the ultrasonic probe 10. The probe head is a portion to be held by the inspector and that accommodates the vibration element array. The magnetic sensor 204 detects the magnetic field generated by the magnetic field generator 202. The positioning controller 206 calculates coordinate information indicating the spatial coordinates of the magnetic sensor 204 on the basis of the detection signal of the magnetic sensor 204. The coordinate information is information that specifies positions on three axes and rotation angles around the three axes. Such coordinate information is sent to the control unit 40. Before the operation of the positioning system 200, calibration is executed. For example, the coordinate system of the positioning system 200 is made to match the coordinate system of the tissue to be subjected to the ultrasonic inspection.

The control unit 40 includes an image analysis unit 208. The image analysis unit 208 is, for example, a machine-learning-type estimator which automatically specifies the site of interest by image analysis. In the step of changing the position and orientation of the probe head of the ultrasonic probe 10, the tomographic images that are sequentially generated are sequentially analyzed by the image analysis unit 208 to automatically identify the site of interest.

On the basis of the position information obtained by the positioning controller 206 and the position information identified by the image analysis unit 208, the position information of the site of interest in the three-dimensional space is calculated. On the basis of the position information, the map generation unit 28 determines the position of the newly added site-of-interest symbol, and the list generation unit 30 generates the newly added site-of-interest record. When the tissue characteristic is identified for the site of interest by the analysis of the image analysis unit 208, the form of the site-of-interest symbol can be determined on the basis of the tissue characteristic, and the findings may be automatically generated.

In the modification, an inspection result table illustrated in, for example, FIG. 11 is generated. In an inspection result table 66A, the coordinate information in an absolute space coordinate system is recorded as the position information 74A (see reference numerals 210, 212, and 214). This coordinate information is converted into coordinate information in the display coordinate system. The display position of the site-of-interest symbol is determined according to the coordinate information. The inspection result table 66A includes image analysis result 216 which includes a category 218 indicating an aspect or a disease level of the site of interest. Thus, the inspection result table may manage various information and, on the basis of the contents of such information, the inspection report may be created.

Figure 12:
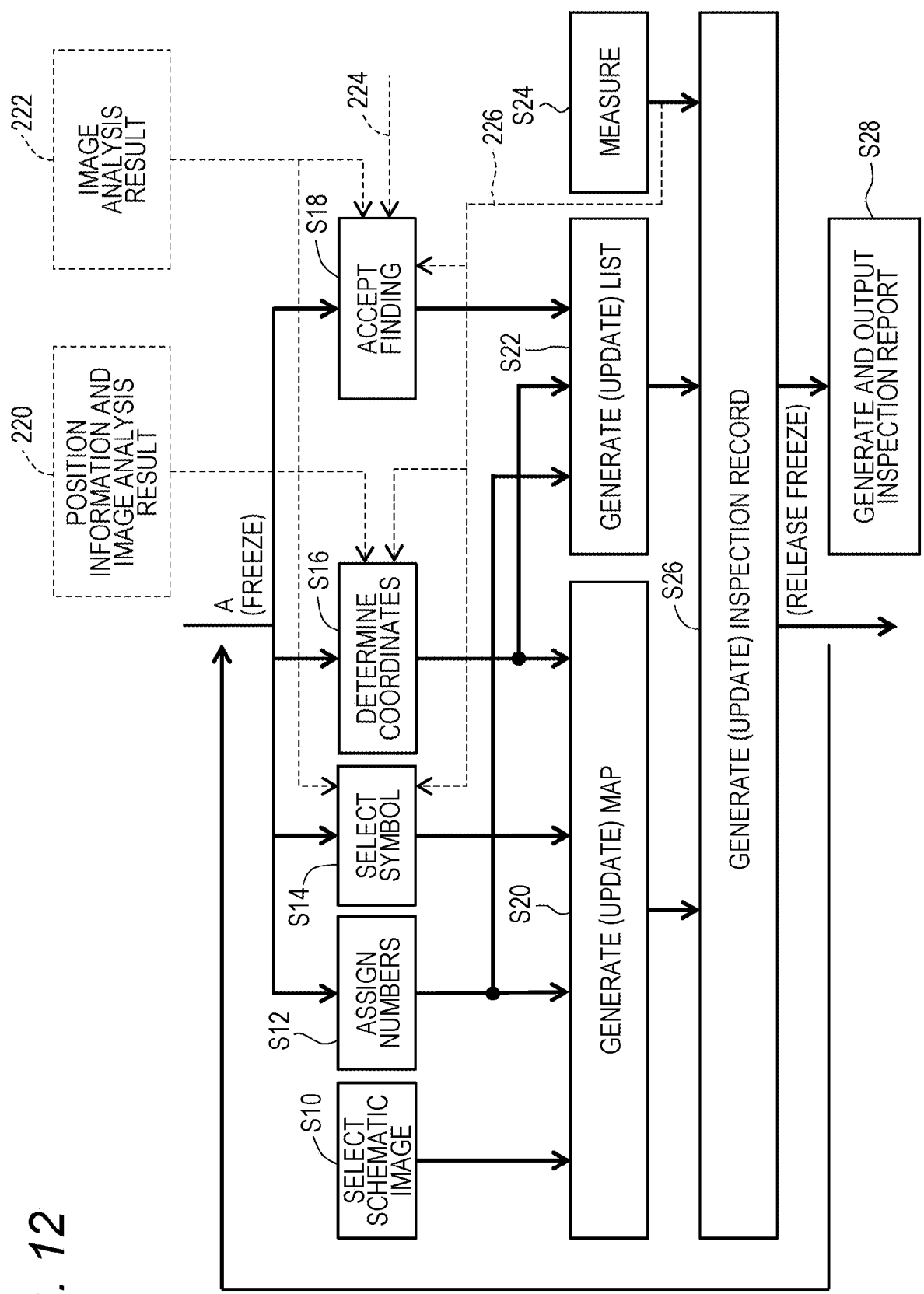
FIG. 12 is a flowchart illustrating an operation of the ultrasonic diagnostic apparatus according to the modification.

FIG. 12 illustrates an operation example of the ultrasonic diagnostic apparatus according to the modification. On the basis of the positioning information and image analysis result 220, the display position of the site-of-interest symbol is determined in S16. On the basis of the image analysis result 222, the findings may be automatically generated and accepted in S18. As indicated by reference numeral 224, other visual evaluation results or other automatic evaluation results may be accepted as findings. For example, an elasticity evaluation result or a blood flow evaluation result of the tissues, and the like, may be recorded as findings.

In S16, the display position of the site-of-interest symbol may be determined on the basis of the measurement result in S24. Alternatively, on the basis of the measurement result in S24, the form of the site-of-interest symbol may be selected in S14. When this modification is adopted, the position of the probe mark is automatically determined as in the determination of the position of the site-of-interest symbol.

In the modified example, it is also possible to provide the record of the individual sites of interest, while performing the ultrasonic inspection, and perform the ultrasonic inspection while referring to the inspection history by then. In particular, the automatically-measured coordinate information and image analysis results are used, so that the burden of the inspector can be further reduced.

Even when the ultrasonic probe is mechanically scanned, the configuration illustrated in each of the above drawings can be adopted. Further, in the case of performing the ultrasonic inspection while reproducing the recorded moving image, the configuration illustrated in the accompanying drawings can be employed. The right breast and the left breast may be distinguished by image analysis.

Multiple ultrasonic inspections may be performed on the same tissue over multiple days and times. In that case, it is easy to reproduce the state of the past ultrasonic inspection by referring to the inspection record recorded in the past. Although the target of the ultrasonic inspection is breast in the above description, the above-described configuration can also be adopted in the ultrasonic inspection of the thyroid gland, the lower limb blood vessel, the carotid artery, heart, and the like.

What is claimed is:

1. An ultrasonic diagnostic apparatus comprising:
a processor configured to:
form an ultrasonic image representing a target tissue in accordance with a reception signal obtained by transmitting and receiving ultrasonic waves to and from the target tissue;
generate an electronic inspection report including a site-of-interest map during execution of an ultrasonic inspection of the target tissue; and
a display having a display screen, the display configured to be communicated with the processor and to display on the display screen the ultrasonic image and the inspection report, wherein
the site-of-interest map includes
a target tissue image representing the target tissue, and
a site-of-interest symbol representing the site of interest identified during the execution of the ultrasonic inspection and displayed on the target tissue image, and
the processor is further configured to
add a new site-of-interest symbol to the site-of-interest map each time a new site of interest is identified during the execution of the ultrasonic inspection, and
determine a position to add the new site-of-interest symbol in accordance with position information indicating a position of the new site of interest.

2. The ultrasonic diagnostic apparatus according to claim 1, wherein
a body mark schematically representing the target tissue and a probe mark schematically representing an ultrasonic probe are displayed along with the ultrasonic image, and
the position information is information indicating a position of the probe mark on the body mark.

3. The ultrasonic diagnostic apparatus according to claim 2, wherein
the ultrasonic image and the inspection report are displayed side by side in a predetermined direction on a screen, and
the body mark and the probe mark are displayed on the side closer to the inspection report of one side or the other side of the ultrasonic image in the predetermined direction.

4. The ultrasonic diagnostic apparatus according to claim 1, wherein
a plurality of symbol forms representing a plurality of tissue characteristics is prepared, and
a specific symbol form corresponding to the tissue characteristic of the site of interest is selected for each site-of-interest symbol from the plurality of symbol forms.

5. The ultrasonic diagnostic apparatus according to claim 1, wherein
the inspection report further includes a site-of-interest list, and
the processor is further configured to add a new site-of-interest report to the site-of-interest list each time a new site of interest is identified during the execution of the ultrasonic inspection.

6. The ultrasonic diagnostic apparatus according to claim 5, wherein the site-of-interest report includes a finding entered by an inspector.

7. A display method for an ultrasonic diagnostic apparatus including a processor, the method comprising:
   forming an ultrasonic image representing a target tissue in accordance with a reception signal obtained by transmitting and receiving ultrasonic waves to and from the target tissue;
   generating an electronic inspection report including a site-of-interest map and a site-of-interest list during execution of an ultrasonic inspection of the target tissue;
   displaying the ultrasonic image and the inspection report;
   adding a new site-of-interest symbol to the site-of-interest map and a new site-of-interest report to the site-of-interest list each time a new site of interest is identified during the execution of the ultrasonic inspection; and
   determining a position to add the new site-of-interest symbol in accordance with position information indicating a position of the new site of interest.

8. A non-transitory computer readable recording medium configured to store a program, which, when executed by a processor of an information processing apparatus, cause operations to be carried out, the operations comprising:
   forming an ultrasonic image representing a target tissue in accordance with a reception signal obtained by transmitting and receiving ultrasonic waves to and from the target tissue;
   generating an electronic inspection report including a site-of-interest map and a site-of-interest list during execution of an ultrasonic inspection of the target tissue;
   adding a new site-of-interest symbol to the site-of-interest map and a new site-of-interest report to the site-of-interest list each time a new site of interest is identified during the execution of the ultrasonic inspection; and
   determining a position to add the new site-of-interest symbol in accordance with position information indicating a position of the new site of interest.

9. The ultrasonic diagnostic apparatus according to claim 2, wherein the processor is further configured to
   display the new site-of-interest symbol at a temporary position, and
   move, from the temporary position, the new site-of-interest symbol in conjunction with subsequent movement of the probe mark.

10. The ultrasonic diagnostic apparatus according to claim 1, wherein the electronic inspection report further includes at least one of an inspection history, information for identifying an inspection site, position information, a measurement value field, a finding field, or a comment field.

11. The ultrasonic diagnostic apparatus according to claim 1, wherein the processor is further configured to analyze the ultrasonic image to automatically identify the new site of interest.

* * * * *